(12) United States Patent
Raju

(10) Patent No.: US 7,858,128 B2
(45) Date of Patent: Dec. 28, 2010

(54) HYDROXYCITRIC ACID COMPOSITIONS, PHARMACEUTICAL AND DIETARY SUPPLEMENTS AND FOOD PRODUCTS MADE THEREFROM, AND METHODS FOR THEIR USE IN REDUCING BODY WEIGHT

(75) Inventor: G. Ganga Raju, Labbipet (IN)

(73) Assignee: Interhealth Nutraceuticals, Inc., Benicia, CA (US)

( * ) Notice: Subject to any disclaimer, the term of this patent is extended or adjusted under 35 U.S.C. 154(b) by 0 days.

(21) Appl. No.: 11/209,580

(22) Filed: Aug. 22, 2005

(65) Prior Publication Data

US 2005/0282904 A1    Dec. 22, 2005

Related U.S. Application Data

(63) Continuation of application No. 09/463,024, filed as application No. PCT/US98/14481 on Jul. 13, 1998, which is a continuation of application No. 08/892,414, filed on Jul. 14, 1997, now abandoned.

(51) Int. Cl.
*A61K 36/00* (2006.01)

(52) U.S. Cl. .................. 424/777; 424/602; 424/610; 424/439; 514/909; 514/574; 514/554

(58) Field of Classification Search .................. None
See application file for complete search history.

(56) References Cited

U.S. PATENT DOCUMENTS

| | | | |
|---|---|---|---|
| 4,354,039 A * | 10/1982 | Guthrie et al. ............... 562/582 |
| 4,490,369 A * | 12/1984 | Reiffen et al. .......... 514/212.07 |
| 5,536,516 A * | 7/1996 | Moffett et al. ............... 426/271 |
| 5,543,405 A | 8/1996 | Keown et al. |
| 5,567,424 A | 10/1996 | Hastings |
| 5,612,039 A | 3/1997 | Policappelli et al. |
| 5,626,849 A | 5/1997 | Hastings et al. |
| 5,656,314 A | 8/1997 | Moffett et al. |
| 5,716,976 A | 2/1998 | Bernstein |
| 5,783,603 A * | 7/1998 | Majeed et al. ............... 514/574 |
| 6,160,172 A | 12/2000 | Balasubramanyam et al. |
| 6,207,714 B1 | 3/2001 | Clouatre et al. |
| 6,217,898 B1 | 4/2001 | Cavazza |
| 6,383,482 B1 | 5/2002 | Gorsek |
| 6,395,296 B1 * | 5/2002 | Balasubramanyam et al. .... 424/439 |
| 6,399,089 B1 | 6/2002 | Yegorova et al. |
| 6,413,545 B1 | 7/2002 | Alviar et al. |
| 6,441,041 B1 | 8/2002 | Clouatre et al. |
| 6,447,807 B1 | 9/2002 | Clouatre et al. |
| 6,476,071 B1 | 11/2002 | Clouatre et al. |
| 6,482,858 B1 | 11/2002 | Clouatre et al. |
| 6,579,866 B2 | 6/2003 | McCleary |
| 6,638,542 B2 | 10/2003 | Nieuwenhuizen et al. |
| 2001/0044469 A1 | 11/2001 | Clouatre et al. |
| 2003/0119913 A1 | 6/2003 | Ohia et al. |
| 2003/0133992 A1 | 7/2003 | Bagchi et al. |
| 2003/0207942 A1 | 11/2003 | Bhaskaran et al. |
| 2004/0014692 A1 | 1/2004 | Bagchi et al. |
| 2004/0157929 A1 | 8/2004 | Ohia et al. |
| 2004/0186181 A1 | 9/2004 | Bagchi et al. |
| 2004/0229953 A1 * | 11/2004 | Gokaraju et al. ............ 514/574 |

FOREIGN PATENT DOCUMENTS

| | | | |
|---|---|---|---|
| WO | WO 96/36585 | * | 11/1996 |
| WO | WO 99/03464 | | 1/1999 |
| WO | WO 00/12080 | | 3/2000 |
| WO | WO 00/48983 | | 8/2000 |
| WO | WO 00/57729 | | 10/2000 |
| WO | WO 02/078616 | | 10/2002 |

OTHER PUBLICATIONS

U.S. Appl. No. 60/554,653, filed Mar. 19, 2004, Bagchi et al.
U.S. Appl. No. 60/628,381, filed Nov. 16, 2004, Bagchi et al.
Clouatre, Dallas, "Anti-Fat Nutrients," Pax Publishing, San Francisco, CA (1993).
Clouatre, Dallas, "New Information on (-)-hydroxycitric acid/HCA," Clouatre Consulting Group (Sep. 5, 1995).
Clouatre, Dallas, et al., "The Diet and health benefits of HCA—How this all-natural diet aid promotes weight loss and inhibits fat production," A Keats Good Health Guide (1994).
Goldberg, Burton, "Weight Loss—An alternative Medicine Definitive Guide," AlternativeMedicine.com Books, Tiburon, California.

(Continued)

*Primary Examiner*—Robert A Wax
*Assistant Examiner*—Hasan S Ahmed
(74) *Attorney, Agent, or Firm*—Marshall, Gerstein & Borun LLP

(57) ABSTRACT

Hydroxycitric acid compositions which comprise approximately 14 to 26% by weight of calcium, and approximately 24 to 40% by weight of potassium or approximately 14 to 24% by weight of sodium, or a mixture thereof, each calculated as a percentage of the total hydroxycitric acid content of the composition, together with dietary supplements and food products containing such compositions and methods for utilizing such compositions, dietary supplements and food products to reduce body weight in mammals are disclosed.

4 Claims, No Drawings

OTHER PUBLICATIONS

Kendall, Pat, "Beware of New Weight Loss Products," Food Science and Human Nutrition Specialist, Colorado State University Cooperative Extension (Jul. 7, 1999).

Ohia, Sunny E., et al., "Safety and mechanism of appetite suppression by a novel hydroxycitric acid extract (HCA-SX)," *Molecular and Cellular Biochemistry*, vol. 238, pp. 89-103, 2002.

Ohia, Sunny E., et al., "Effect of Hydroxycitric Acid on Serotonin Release from Isolated Rat Brain Cortex," Research Communications in Molecular Pathology and Pharmacology, vol. 109, Nos. 3 & 4, Mar., Apr. 2001, pp. 210-216.

Palmeri, Denise, "Metabolife, Metabolite and Chitoslim: Safe Bets for Losing Weight?," ext.colostate.edu, May 2002 pp. 1-4.

Romsos, Chee H., "Influence of (-)-hydroxycitrate on lipigenesis in chickens and rat," http://www.ncbi.nlm.nih.gov.

Roy, Sashwati, et al., "Body Weight and Abdominal Fat Gene Expression Profile in Response to a Novel Hydroxycitric Acid-Based Dietary Supplement," *Gene Expression*, vol. 11, pp. 251-262, Feb. 24, 2004.

Shara, Michael, et al., "Physico-chemical properties of a novel (—)-hydroxycitric acid extract and its effect on body weight, selected organ weights, hepatic lipid peroxidation and DNA fragmentation, hematology and clinical chemistry, and histopathological changes over a period of 90 days," *Molecular and Cellular Biochemistry*, vol. 260, pp. 171-186, Oct. 3, 2003.

Verghese, James, "(-)-Hydroxycitrates—The usefulness of (-)-hydroxycitric acid as an obesity regulator is attracting more attention from the food & pharmaceutical industry. Can it be called an ingredient for functional foods?," The World of Ingredients.

Wong, Cathy, "Evaluating Natural Weight Loss Supplements, What to Try and What to Avoid," http://altmedicine.about.com/library/weekly; pp. 1-8, printed May 16, 2002.

AIM Metabolite (1999) AIM International, Inc.

Clinical Study on Ephedra-Free Super Citrimax®; Interhealth, dated Jan. 29, 2004. Press Release.

Herbs and Weight Loss FAQ's; http://herbsforhealth.about.com/library, pp. 1-3.

Researchers Reveal the Beauty of Super CitriMax®—Again; New HCA Study Confirms Super CitriMax® may be the most Effective, All-Natural Diet Ingredient Yet. pp. 1-8.

* cited by examiner

HYDROXYCITRIC ACID COMPOSITIONS, PHARMACEUTICAL AND DIETARY SUPPLEMENTS AND FOOD PRODUCTS MADE THEREFROM, AND METHODS FOR THEIR USE IN REDUCING BODY WEIGHT

PRIORITY CLAIM

This application is a continuation of U.S. patent application Ser. No. 09/463,024, titled: Hydroxycitric Acid Compositions, Pharmaceutical and Dietary Supplements and Food Products Made There from, and Methods For Their Use In Reducing Body Weight, inventor: G. Ganga Raju, filed Feb. 15, 2002 which claims priority to PCT application PCT/US98/14481 titled: Hydroxycitric Acid Compositions, Pharmaceutical and Dietary Supplements and Food Products Made Therefrom, and Methods For Their Use In Reducing Body Weight, inventor: G. Ganga Raju, filed Jul. 13, 1998, which claims priority to U.S. patent application Ser. No. 08/892,414, titled: Hydroxycitric Acid Compositions, Pharmaceutical and Dietary Supplements and Food Products Made There from, and Methods For Their Use In Reducing Body Weight, inventor: G. Ganga Raju, filed Jul. 14, 1997. These applications are herein incorporated by reference in their entirety.

CROSS REFERENCE TO RELATED APPLICATIONS

This application is related to the following application, which was filed of even date herewith:

"Hydroxycitric Acid Compositions, Pharmaceutical and Dietary Supplements and Food Products Made Therefrom, and Methods For Their Use In Reducing Body Weight," by G. Ganga Raju, Attorney Docket No. IHEAL-01063US2 SRM/AGC.

BACKGROUND OF THE INVENTION

Hydroxycitric Acid has been known for many years to be beneficial for the control and reduction of mammalian body weight. In particular, a specific stereoisomer of hydroxycitric acid, the (−)hydroxycitric acid isomer and derivatives thereof, is known to inhibit fatty acid and cholesterol synthesis and to function as a natural anorectic agent in mammals.

The stereoisomers of hydroxycitric acid are related structurally to citric acid wherein a hydroxy group is substituted for one of the four methylene hydrogens. Thus, there are four possible stereoisomers of hydroxycitric acid. Of these four stereoisomers, the (−) hydroxycitric acid isomer has been found to substantially inhibit fatty acid synthesis in biological systems in profused organs and intact mammals, and particularly in non-ruminant mammals.

It has also been known that the particular stereoisomer of interest, in both free acid and lactone forms, is found in the rind of the fruits of *Garcinia* species, for example, *Garcinia cambogia, Garcinia atroviridis* and *Garcinia indica*, which are native to the Indian subcontinent. The hydroxycitric acid component can be obtained by isolation from the fruit of *Garcinia* species using known procedures, for example Lewis, Y. S. "Methods in Enzymology" (J. M. Lowenstein, Ed., Vol. 13, pg. 613) (Academic Press, N.Y. 1969), and U.S. Pat. No. 5,536,516.

As an inhibitor of the synthesis of fatty acids and cholesterol, hydroxycitric acid has been shown to significantly reduce the body weight and lower lipid accumulation in rats. See, e.g. Sergio, W. Medical Hypothesis 27:39 (1988), Sullivan, A. C., et al., Lipids 9:121(1973), and Sullivan, A. C., et al., Lipids 9:129 (1973).

However, in order to formulate the compositions containing hydroxycitric acid into dietary supplements and food products, a number of desirable properties are sought. First, as most such supplements and food products are administered orally, the composition should have negligible odor and taste. Second, in order to increase the bioavailability of the hydroxycitric acid, the composition should be soluble in water.

Solubility in water, as well as clarity in solution, are also important properties in many food and beverage applications. In addition, it is highly desirable that the composition be non-hygroscopic, in order to facilitate storage and formulation into dietary supplements and food products. Another desirable property is the hydroxycitric acid potency of the composition, where high potency levels are desirable.

SUMMARY OF THE INVENTION

The present invention provides hydroxycitric acid compositions, food products made therefrom and methods for their use in reducing body weight.

In one aspect, the invention provides a hydroxycitric acid composition for reducing body weight wherein the composition comprises approximately 14 to 26% by weight of calcium, and approximately 24 to 40% by weight of potassium or approximately 14 to 24% by weight of sodium, or a mixture thereof, calculated as a percentage of the total hydroxycitric acid content of said composition.

In another aspect of the invention, a composition for reducing body weight is provided which comprises at least approximately 40% by weight of total hydroxycitric acids which further comprise approximately 5 to 13% by weight of calcium, and approximately 9 to 20% by weight of potassium or approximately 5 to 12% by weight of sodium, or a mixture thereof, calculated as a percentage of the total weight of said composition.

Additional aspects of the invention include dietary supplements and food products for use in reducing body weight which include the present compositions, and methods for reducing body weight by administering such compositions, dietary supplements and food products to mammals.

DETAILED DESCRIPTION OF THE INVENTION

Hydroxycitric acid has been known for years to be useful for inhibiting fatty acid synthesis. Citrate is formed in the mitochondria by the citrate synthase reaction.

It is then metabolized via the citric acid cycle. Under certain metabolic conditions, some citrate is diverted to the cell cytosol where it is used for fatty acid synthesis, that is, for energy storage. The inhibition of fatty acid synthesis in biological systems by the use of hydroxycitric acid is believed to arise from the inhibition of the citrate cleavage enzyme citrate-lyase by such compounds. The cleavage of citrate is catalyzed by citrate-lyase and citrate is the major source of the acetyl group of acetyl coenzyme A which is utilized in the conversion of carbohydrates and various amino acids to fats by non-ruminant mammals.

Typically, hydroxycitric acid is utilized in the form of its pharmaceutically acceptable, non-toxic basic salts. Such salts include, for example, the alkali metals, e.g. sodium and potassium, the alkaline earth metals, e.g. calcium and magnesium, and complex salts, such as ammonium or substituted ammonium salts.

In preparing various salts of hydroxycitric acid, it has been found that the pure potassium salt was highly soluble in water, but possessed high hygroscopicity, an undesirable property. It was also determined that the pure calcium salt was moderately soluble in water, and possessed minimal hygroscopicity, a desirable property.

Surprisingly, it has been determined that a mixture of calcium salt with potassium or sodium salts produces a composition which is highly soluble (up to 25% weight to volume in water), but with minimal hygroscopicity.

Furthermore, the composition according to the present invention displays minimal palatability concerns, as the taste of free hydroxycitric acid is almost entirely eliminated, as well as exceptional product application properties, including negligible odor, taste and color. While normally brown, the composition was found to be clear in solution.

In addition, the composition was found to be largely free of the lactone form of hydroxycitric acid, and that in solution it did not equilibrate between the free and lactone forms. Further desirable properties included a balanced pH, and a low (<1%) sodium content. Although sodium is an acceptable replacement for potassium in the present compositions, its inclusion is considered undesirable for considerations of minimizing dietary intake.

Thus the present compositions demonstrate a surprising, synergistic relationship between the calcium content and the potassium (or sodium) content. It has been determined that for a composition where the total hydroxycitric acid content exceeds 40% by weight, a total of salts of hydroxycitric acid which desirably comprise approximately 5 to 13% by weight of calcium, preferably approximately 7 to 13%, and approximately 9 to 20% by weight of potassium, preferably approximately 14 to 18%, or approximately 5 to 10% by weight of sodium, or mixtures of potassium and sodium.

As stated earlier, although sodium is acceptable, it is considered desirable to minimize the content of sodium, desirably to less than 1% by weight.

It is further considered desirable to provide a composition in which the total hydroxycitric acid content is at least approximately 40% by weight, preferably at least approximately 50%, and desirably approximately 55-65%. Thus, in another aspect of the invention, a composition for reducing body weight is provided which comprises at least approximately 50% by weight of total hydroxycitric acids which further comprise approximately 5 to 13% by weight of calcium, and approximately 9 to 20% by weight of potassium or approximately 7 to 12% by weight of sodium, or a mixture thereof, calculated as a percentage of the total weight of said composition. Of the total amount, it is also considered desirable that the amount of hydroxycitric acid in the form of the lactone not exceed approximately 2% by weight.

It is considered desirable to enrich the purity of free hydroxycitric acid from the *Garcinia* rind and prepare a calcium salt of the hydroxycitric acid. Generally, commercially available *Garcinia* rind comprises 25 to 30% moisture and 2 to 5% of sodium chloride. *Garcinia* rind contains 10 to 12% of free hydroxycitric acid, 12 to 15% of the lactone form of hydroxycitric acid and 2 to 3% citric acid on dry weight of the rind.

A further aspect of the preparation of the salt of hydroxycitric acid is to mask the sour taste of hydroxycitric acid, minimize the percentage of hydroxycitric acid lactone and prepare a sodium free salt of hydroxycitric acid. The process generally comprises washing the *Garcinia* rind, extracting hydroxycitric acid from the *Garcinia* rind, preparing an insoluble calcium salt of the hydroxycitric acid, dissociating the insoluble calcium salt and thereafter preparing calcium and potassium salts of hydroxycitric acid. The washing of the *Garcinia* rind is optional, as the sodium chloride can be reduced at other stages in the processing.

The salt free water extract can be obtained from salted *Garcinia* rind by washing the *Garcinia* rind followed by hot extraction. The dilute water extract is filtered through a filtrate after adding clay to the extract and settled. The filtered dilute extract is then concentrated to 45% total solids under reduced pressure at elevated temperature.

This concentrate contains 10 to 12% of free hydroxycitric acid by weight, 11 to 13% of hydroxycitric acid lactone by weight and 2 to 3% of citric acid by weight.

The content of free hydroxycitric acid, hydroxycitric acid lactone, citric acid and non acid solutes can be determined by known techniques.

The process of enriching free hydroxycitric acid from the rind is accomplished by preparing a water extract of the rind, converting the extract into a insoluble calcium citrate and removing non acidic impurities in the extract, such as pectin, sugar and color which will solubilize, by washing the calcium hydroxycitrate. Thereafter, the calcium hydroxycitrate is dissociated with dilute phosphoric acid to form hydroxycitric acid and calcium phosphate. The calcium phosphate is then filtered out and the enriched hydroxycitric acid solution is converted to highly soluble calcium salt by first adjusting the pH of the hydroxycitric acid solution to 3.5 to 5 with calcium hydroxide suspension and second by the addition of potassium hydroxide solution to adjust the final pH to 8.0 to 9.0. This calcium salt solution is then filtered and concentrated under reduced pressure to approximate 50% total solids. The concentrate is then treated with 75% alcohol/acetone to crystallize white crystalline highly soluble calcium salt.

There are numerous protocols available for preparing hydroxycitric acid extracts from *Garcinia* fruits. The rind of the *Garcinia* fruit which is commercially available typically consists of approximately 20% hydroxycitric acid, approximately 25% moisture and approximately 2.5% sodium chloride. It is considered desirable to eliminate as much sodium chloride from the rind as possible and since sodium chloride is freely soluble in water, this is easily accomplished. For example, one kilogram of raw *Garcinia* rind material is washed with approximately 2 liters of water in a stainless steel vessel. Thereafter, salt free *Garcinia* rind is extracted with 55 to 60"C water on a continuing basis with approximately 15 liters of water. The spent rind is then tested for hydroxycitric acid content and typically discarded. At this stage, recovery of total hydroxycitric acid is on the order of 90+2%.

Next, approximately 2.5 kilograms of Fuller's Earth (a kaolin containing an aluminum magnesium silicate) is added to the solution obtained previously. The mixture is stirred for one hour with continuous agitation at approximately 100 revolutions per minute then allowed to settle for two hours. Thereafter, the material is filtered through a bed of a filter aid in a centrifuge. The filtrate is concentrated to 800 grams of approximately 45% total solids containing approximately 22% total hydroxycitric acid content. The yield at this step is approximately 97% of the extracted hydroxycitric acid.

Next, the concentrated extract is filtered in a centrifuge to remove solids. To the filtered extract is added calcium hydroxide (100 grams in 500 ml of water). The mixture is stirred for approximately four hours maintaining the pH of the solution at approximately 8.5. Thereafter, the mixture is filtered through the centrifuge and the supernatant is discarded. The moist pellet is washed continuously with 5 liters of water until the water is colorless and no solids are extracted from the filtrate. The yield of hydroxycitric acid at this phase is approximately 96.5%. In the next step, the wet pellet of calcium hydroxycitrate obtained previously is treated with 500 ml of 2N phosphoric acid solution to convert the calcium hydroxycitrate to hydroxycitric acid and calcium phosphate. Calcium phosphate precipitate is removed by centrifugation and washed with 2 liters of water. The filtrate contains approximately 165 grams of hydroxycitric acid with total solids of approximately 6.8% and the hydroxycitric acid yield is approximately 91.6%.

Finally, the hydroxycitric acid solution obtained previously is treated with calcium hydroxide (61.7 grams in 600 ml of water to adjust to pH 4.5). This solution is treated with neutral charcoal (60 grams at 75° C. for two hours under agitation, cooled and filtered). To the filtrate is added potassium hydroxide (52 grams in 50 ml of water), which adjusts the pH to between 8.0 and 8.5. This salt solution is concentrated to 555 grams under reduced pressure to provide 50% total solids. The concentrate is treated with 75% acetone to obtain pure crystalline highly soluble calcium salt of hydroxycitric acid.

The amount of (−) hydroxycitric acid can be estimated by high pressure liquid chromatography (HPLC), generally as follows.

Estimation of (−) HCA by HPLC:
HPLC System: SHIMADZU or equivalent
LC 1OAT Pump or equivalent
SPD 10 Detector or equivalent
CR 10A Software or equivalent
Column: ALLTIMA C,2(5,u) (4.6×250 mm)
Wave Length: 210 nm
Flow rate: 1 mL/min
Volume of Injection: 20 kL
Temperature: 25+2 C.
Mobile Phase: 0.05M sodium sulphate solution in water (pH adjusted to approximately 2.3 with conc. H2SO4).
Standards: 1) Ethylenediamine Salt of (−) HCA.

2) (−) HCA Lactone.
Standards Preparation: Weigh accurately about 50 mg of each standard into two different 25 mL volumetric flasks. Dissolve in water and make up to volume with water. Filter through 0.22,u membrane filter and inject the standard solutions separately.

Sample preparation: Weigh accurately about 50 mg of sample in a 25 mL volumetric flask. Dissolve it in water and make up the volume with water.

Filter through 0.22,u membrane filter and inject the solution.

Retention Times: for free (−) HCA −5 min.

(−) HCA Lactone −4.1 min.
Calculations: % of Free (−) HCA=Sample Area×Standard Conc.×Purity of Standard Standard Area×Sample Conc.
% of (−) HCA Lactone=Sample Lactone Area×Lactone Standard Conc.×Purity of Lactone
Lactone Standard Area×Sample Conc.
REAGENTS
Unless otherwise stated all chemicals used are reagent grade. All glass washed with double distilled water.
Dilute ammonia solution, 25% w/v.
Ammonium chloride.
EDTA
Mordant Black T mixture
Sodium sulphate, analytical grade, or equivalent
Sulphuric acid, analytical grade or equivalent
WATER SOLUBLE EXTRACTIVES: As per USP XX.

As per USP (1% Solution)
MOISTURE CONTENT As per USP (K.F. Titrimeter)
CALCIUM: Weigh accurately about 10 mg of sample into a 100 mL conical flask, dissolve it in 50 mL of water. Add 2 mL of ammonia—ammonium chloride (pH 9.2) buffer. Then titrate with 0.01M EDTA solution.
Using Mordant Black-T Mixture as indicator. End point is blue.
% of Calcium=Titre value×Molarity of EDTA×0.4×100
0.01×Weight of the sample in mg.

Estimation of Sodium and Potassium by Flame Photometer:
Place 100 mg of sample in a Silica crucible, and reduce to ash in a muffle furnace at 400"C. Transfer ash into a 50 mL volumetric flask, add 1 drop conc. HCl and water to dissolve and make up to volume with water.

Calibrate the flame photometer with 100, 50 and 10 pom standard sodium and potassium solutions. Now place the sample solution in the flame photometer. Note the ppm reading corresponding to Sodium and Potassium.

% of corresponding Ion=ppm reading corresponding Ion× 50×100 1000×Weight of sample in mg.

By inhibiting the synthesis of fatty acids, hydroxycitric acid is useful for the reduction of body weight in mammals. These useful compositions can be provided in the form of conventional pharmaceutical preparations or dietary supplements, for example, they can be mixed with conventional organic or inorganic inert pharmaceutical carriers or dietary supplements suitable for oral or parenteral administration, such as, for example, water, gelatin, lactose, starch, magnesium stearate, talc, vegetable oil, gums or the like. They can be administered in conventional forms, e.g., solid forms, for example powders, tablets, capsules, suppositories or the like; or in liquid forms, for example, suspensions or emulsions. In addition, such compositions can be formulated as a part of a processed food product for example in a form of a bar, baked good, beverage and the like.

Moreover, the pharmaceutical compositions and dietary supplements can be subject to conventional pharmaceutical or dietary supplements expedients, such as sterilization, and can contain conventional pharmaceutical or dietary supplements excipients, such as preservatives, stabilizing agents, emulsifying agents, salts for the adjustment of osmotic pressure or buffers, and the like. The compositions can also contain other therapeutically active materials.

A suitable dosage unit will typically contain from about 15 to about 3000 mg of hydroxycitric acid, administered up to three times per day. Suitable parenteral dosage regimens in mammals can comprise from about 1 mg per kilogram of body weight to about 50 mg per kilogram of body weight per day. However, for any particular subject, the specific dosage regimen should be adjusted according to individual need and the professional judgment of the person administering or supervising the administration of the aforesaid compounds.

Additional aspects of the invention include food products and the like for use in reducing body weight which include the present compositions, and methods for reducing body weight by administering such compositions and dietary supplements and food products. When provided for oral administration as a processed food product, such as a beverage or a snack bar, the hydroxycitric acid content will desirably comprise approximately 0.001 to 25%, preferably 0.05 to 5% by weight of the total weight of the food product.

Preparation of processed food products to include hydroxycitric acid compositions of the present invention involves, for example, diluting a concentrate of the composition containing at least approximately 40% hydroxycitric acid in water, adding supplements, blending, heating and/or periodic agitation.

For both snack bars and beverages, it is desirable to pre-pasteurize the concentrate in a highly diluted ratio with purified water. For example, approximately 1 mL of the concentrate can be added to 12 fluid ounces of water. These figures will however vary depending upon the types of products desired, ranging from 1 to 25% for a beverage and 1 to 40% for a snack bar. After the blending step, the temperature of the vessel which the preprocessing step takes place is increased, frequently using steam as in the case of beverage manufacture or low heat as in the case of snack bars and baked goods. Before heat is applied, materials such as nutrients, antioxidants, vitamins and minerals can be added. In the production of the beverage, after the supplementation of the desired additives and achievement of homogeneosity, the liquid is pumped by a stainless steel pipeline into a bottling facility. High temperature steam is applied from the outside to the pipes which in turn maintains the temperature of the liquid during its transit. The pipes are placed so as to facilitate the bottling of the liquid beverage in an efficient manner.

In the preparation of, for example, snack bars, the preprocessing follows approximately the same protocol as for beverages. The environment for the development of this product is typically an industrial kitchen with the use of large cooking pots. The diluted hydroxycitric acid composition is blended with water, covered and heated, bringing it to a boil for a certain period of time. This boiling also provides agitation to insure thorough mixing. Thereafter, snack bars, baked goods or other processed food products are produced in accordance with the techniques well known in the art.

All patents and patent applications cited in this specification are hereby incorporated by reference as if they had been specifically and individually indicated to be incorporated by reference.

Although the foregoing invention has been described in some detail by way of illustration and example for purposes of clarity and understanding, it will be apparent to those of ordinary skill in the art in light of the disclosure that certain changes and modifications may be made thereto without departing from the spirit or scope of the appended claims.

I claim:

1. A process of producing potassium calcium salt of hydroxycitric acid from the rind of *Garcinia* fruit comprising:
    (a) preparing a water extract of the *Garcinia* rind;
    (b) precipitating one or more hydroxycitric acid salts out of the water;
    (c) adding an acid;
    (d) adding calcium hydroxide to adjust to between:
    a lower limit of approximately pH 3.5; and
    an upper limit of approximately pH 5; to form calcium hydroxycitric acid; and
    (e) adding potassium hydroxide to adjust to between:
    a lower limit of approximately pH 8; and
    an upper limit of approximately pH 9; to form potassium calcium hydroxycitric acid.

2. The process of claim 1, where in step (a) further comprises decolorizing the water extract with a third reagent.

3. The process of claim 2, wherein the third reagent is selected from the group consisting of Fuller's Earth, kaolin and aluminum magnesium silicate.

4. The process of claim 1, wherein the acid is phosphoric acid; wherein the phosphoric acid is added to re-dissolve the precipitated hydroxycitric acid salts forming insoluble phosphate-salts.

* * * * *

UNITED STATES PATENT AND TRADEMARK OFFICE
CERTIFICATE OF CORRECTION

PATENT NO. : 7,858,128 B2
APPLICATION NO. : 11/209580
DATED : December 28, 2010
INVENTOR(S) : G. Ganga Raju Page 1 of 2

It is certified that error appears in the above-identified patent and that said Letters Patent is hereby corrected as shown below:

In the Specification:

At column 5, line 32, replace "20kL" with --20μL--;

At column 5, line 33, replace "25 +2C" with --25° ± 2° C--;

At column 5, line numbers 25-37, immediately after "Estimation of (-) HCA by HPLC:", replace the lines of text with the following table:

| | |
|---|---|
| HPLC System: | SHIMADZU or equivalent |
| | LC 10AT Pump or equivalent |
| | SPD 10 Detector or equivalent |
| | CR 10A Software or equivalent |
| Column: | ALLTIMA $C_{12}(5\mu)$ (4.6 x 250 mm) |
| Wave Length: | 210 nm |
| Flow rate: | 1mL/min |
| Volume of Injection: | 20 μL |
| Temperature: | 25° ± 2° C. |
| Mobile Phase: | 0.05M sodium sulphate solution in water (pH adjusted to approximately 2.3 with conc. $H_2SO_4$ |
| Standards: | 1) Ethylenediamine Salt of (-) HCA. |
| | 2) (-) HCA Lactone |

--;

At column 5, line numbers 41 and 46, replace ",u" with --μ--;

Signed and Sealed this
First Day of April, 2014

Michelle K. Lee
*Deputy Director of the United States Patent and Trademark Office*

CERTIFICATE OF CORRECTION (continued)
U.S. Pat. No. 7,858,128 B2

In the Specification, continued:

At column 5, line numbers 51-55, replace the lines of text with the following equations:

--Calculations:

$$\% \text{ of Free (-) HCA} = \frac{\text{Sample Area} \times \text{Standard Conc.} \times \text{Purity of Standard}}{\text{Standard Area} \times \text{Sample Conc.}}$$

$$\% \text{ of (-) } HCA \text{ Lactone} = \frac{\text{Sample Lactone Area} \times \text{Lactone Standard Conc.} \times \text{Purity of Standard}}{\text{Lactone Standard Area} \times \text{Sample Conc.}}$$

--;

At column 5, line number 67- column 6, line 8, replace the lines of text with the following table:

| | |
|---|---|
| WATER SOLUBLE EXTRACTIVES: | As per USP XX. |
| pH: | As per USP (1% Solution) |
| MOISTURE CONTENT: | As per USP (K.F. Titrimeter) |
| CALCIUM: | Weigh accurately about 10 mg sample into a 100 mL conical flask, dissolve it in 50mL of water. Add 2mL of ammonia-ammonium chloride (pH 9.2) buffer. Then titrate with 0.01M EDTA solution. Using Mordant Black-T Mixture as indicator: End point is blue. |

--;

At column 6, line numbers 9-10, replace the lines of text with the following equation:

$$\% \text{ of Calcium} = \frac{\text{Titre value} \times \text{Molarity of EDTA} \times 0.4 \times 100}{0.01 \times \text{Weight of the sample in mg.}}$$

--;

At column 6, line numbers 21-22, replace the lines of text with the following equation:

$$\% \text{ of corresponding Ion} = \frac{\text{ppm reading corresponding Ion} \times 50 \times 100}{1000 \times \text{Weight of the sample in mg.}}$$

--.